United States Patent
Brown et al.

(10) Patent No.: US 7,490,047 B2
(45) Date of Patent: Feb. 10, 2009

(54) APPARATUS AND METHOD FOR CONSTRUCTING FORMULARIES

(75) Inventors: Kenneth J. Brown, Yorktown Heights, NY (US); William D. Tobin, Franklin Lakes, NJ (US); Glen D. Stettin, Upper Saddle River, NJ (US); Roselin Daniel, Randolph, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 898 days.

(21) Appl. No.: 10/337,366

(22) Filed: Jan. 7, 2003

(65) Prior Publication Data

US 2004/0006491 A1   Jan. 8, 2004

Related U.S. Application Data

(60) Provisional application No. 60/349,407, filed on Jan. 22, 2002.

(51) Int. Cl.
G06Q 50/00    (2006.01)
G06Q 40/00    (2006.01)

(52) U.S. Cl. ............................................ 705/2; 705/4
(58) Field of Classification Search ................. 705/2–4
See application file for complete search history.

(56) References Cited

U.S. PATENT DOCUMENTS

| | | | | |
|---|---|---|---|---|
| 4,847,764 | A | * | 7/1989 | Halvorson ................... 700/231 |
| 5,737,539 | A | * | 4/1998 | Edelson et al. .................. 705/3 |
| 5,758,095 | A | * | 5/1998 | Albaum et al. .................. 705/2 |
| 5,845,255 | A | | 12/1998 | Mayaud |
| 5,950,630 | A | | 9/1999 | Portwood et al. |
| 6,067,524 | A | | 5/2000 | Byerly et al. |
| 6,104,398 | A | * | 8/2000 | Cox et al. .................... 715/821 |
| 6,240,394 | B1 | | 5/2001 | Uecker et al. |
| 6,282,531 | B1 | | 8/2001 | Haughton et al. |
| 6,314,556 | B1 | * | 11/2001 | DeBusk et al. ............... 717/107 |
| 6,317,719 | B1 | * | 11/2001 | Schrier et al. ................... 705/2 |
| 6,356,873 | B1 | | 3/2002 | Teagarden et al. |
| 6,542,902 | B2 | * | 4/2003 | Dulong et al. ............ 707/104.1 |
| 6,694,334 | B2 | * | 2/2004 | DuLong et al. .......... 707/104.1 |
| 2001/0037216 | A1 | * | 11/2001 | Oscar et al. ..................... 705/2 |

(Continued)

OTHER PUBLICATIONS

David J. Gross, Prescription drug formularies in managed care: concerns for the elderly population, Nov.-Dec. 1998, Clinical Therapeutics, vol. 20, Issue 6, pp. 1277-1291.*

(Continued)

*Primary Examiner*—C Luke Gilligan
*Assistant Examiner*—Tran Nguyen
(74) *Attorney, Agent, or Firm*—Irah H. Donner; Wilmer Cutler Pickerin Hale and Dorr LLP

(57) ABSTRACT

A system for constructing formularies is disclosed. The system includes a central computer system and at least one additional computer. The central computer system compiles a list of various pharmaceutical products and sorts them into different categories based on predetermined relational characteristics. The relational characteristics are based on therapeutic classifications of the pharmaceutical products, which in turn share these relational characteristics. Formularies are then created by selecting individual products and/or categories of products that the formularies would support. When prescription claims are received, coverage is either accepted or denied based on whether the products in die prescription claims are covered by the formulary.

36 Claims, 13 Drawing Sheets

U.S. PATENT DOCUMENTS

| | | | |
|---|---|---|---|
| 2001/0049673 A1* | 12/2001 | Dulong et al. | 707/1 |
| 2002/0138303 A1* | 9/2002 | Enos et al. | 705/2 |
| 2002/0143579 A1 | 10/2002 | Docherty et al. | |
| 2003/0172081 A1* | 9/2003 | Dulong et al. | 707/100 |

OTHER PUBLICATIONS

C. Michael Stein, MD et al., Implementation of multiple outpatient formularies: undesirable effects, Jan. 1997, Clinical Pharmacology & Therapeutics, vol. 1, No. 1, pp. 1-7.*

Kessler D, Rose JL, Temple RJ, et al. Therapeutic-class wars—Drug promotion in a competitive marketplace. NEJM. 1994; 331:1350-1353.*

Isacson, Drugs up in smoke: a study of caseated drugs in Sweden, Apr. 1999, Pharmacy World & Science; ; 21, 2; Health & Medical Complete p. 96-99.*

The Merck Manual, 1899, Merck & Co., p. 185.*

The Merck Manual, 1992, Merck & Co., p. 2602.*

Cushny, A text-book of Pharmacology and Therapeutics, 1934, Lea & Febiger, p. vii-x.*

Barrett, An intranet-based formulary management system, May 1, 200, American Society of Health-System Pharma, 57(9):907-8.*

S. Levine et al., "Kaiser Permanente's Prescription Drug Benefit," Health Affairs 19, No. 2 (2000): 185-190.*

Snow, Bonnie, EMBASE Update for the Pharmaceutical Searcher Database; Dec. 1991; 14, 6; ABI/INFORM Global☐☐p. 93-96.*

Pahor, Drug data coding and analysis in epidemiologic studies, Aug. 1994, Eur J Epidemiol, 10(4):405-11.*

Grabowski, Pharmacy benefit management, cost-effectiveness analysis and drug formulary decisions, Aug. 1997, Social Science & Medicine, The Impact of Cost-Effectiveness on Public and Private Policies in Health Care: An International Perspective, vol. 45, Issue 4, pp. 535-544.*

Carruthers, A novel formulary: collaboration between health care professionals, seniors, private sector and government in Nova Scotia, Jul. 13, 1999, Canadian Medical Association, vol. 161, Issue 1, p. 58-61.*

Goldberg, Managing the Pharmacy Benefit: The Formulary System, 1997, Journal of Managed Care Pharmacy, vol. 3, p. 565-573.*

Fijn, The quality of Dutch hospital drug formularies: Evaluation of technical features and organisational information, Jun. 1999, Pharmacy World and Science, vol. 21, No. 3, p. 120-126.*

Sep. 23, 2003. PCT International Search Report for PCT/US03/01650.

Written Opinion for International Application No. PCT/US03/01650 mailed Nov. 3, 2004.

International Preliminary Examination Report, Application No. PCT/US03/01650 mailed Mar. 14, 2005.

* cited by examiner

FLEXIBLE MERCK-MEDCO ELECTRONIC DRUG SYSTEM

FILE  MAINTENANCE  REPORTS  HELP

STATIC FORMULARY INFORMATION

SAVE  CLEAR  CANCEL  CONTINUE — 140

| GENERAL INFO. | MEDCO CONTACT INFO. | MAINTENANCE QUESTIONS | PREFERRED ALTERNATIVE ID | ADMIN. ID |

FORMULARY NAME: _____

FORMULARY ID: _____

CLIENT NAME: _____

CLIENT CONTACT NAME: _____

P&T DECISION MADE BY: MEDCO ▼

CLIENT MEET FOR P&T DECISIONS: NEVER ▼

REBATE COLLECTION: MEDCO ▼

APPROXIMATE LIVES COVERED: INDIVIDUAL ▼

ACCOUNT TYPE:
○ RETAIL ONLY
○ MAIL ONLY
● INTEGRATED

○ MODEL FROM STANDARD FORULARY
○ MODEL FROM EXISTING FORMULARY
○ CREATE NEW

BASE FORMULARY: MED ▼

FORMULARY DESCRIPTION: _____

FORMULARY COMMENTS: _____ — 148

STATUS: W/P ▼

INSTALLATION DATE: — 146

JANUARY  2000
| S | M | T | W | T | F | S |
|---|---|---|---|---|---|---|
| 26 | 27 | 28 | 29 | 30 | 31 | 1 |
| 2 | 3 | 4 | 5 | 6 | 7 | 8 |
| 9 | 10 | 11 | 12 | 13 | 14 | 15 |
| 16 | 17 | 18 | 19 | 20 | 21 | 22 |
| 23 | 24 | 25 | 26 | 27 | 28 | 29 |
| 30 | 31 | 1 | 2 | 3 | 4 | 5 |

JANUARY 2, 2000

LAST MODIFIED BY USER: _____

LAST MODIFIED DATE: _____

FRS - [DB0PFCT0] - [TREEVIEW (FORMULID=35)]

FILE  MAINTENANCE  REPORTS  HELP

SAVE | CLEAR ALL | EXIT | DISPLAY MODE  TREE VIEW ONLY ▼ | HIDE BLOCK ATTRIBUTES | ✚

FORMULARY BLOCKS                                    FORMULARY FLAGS
01:00:00:00 ANTI INFECTIVES
02:00:00:00 ANTINEOPLASTIC 7 IMMUNOSUPPRESSANT DRUGS
03:00:00:00 AUTONOMIC & CNS DRUGS, NEUROLOGY & PSYCH
04:00:00:00 CARDIOVASCULATR, HYPERTENSION & LIPIDS
05:00:00:00 DERMATOLOGICAL TOPICAL THERAPY
06:00:00:00 EAR, NOSE & THROAT MEDICATIONS
07:00:00:00 ENDOCRINE/DIABETES
08:00:00:00 GASTROENTEROLOGY
09:00:00:00 IMMUNOLOGY, VACCINES & BIOTECHNOLOGY
10:00:00:00 MUSCULOSKELETAL & RHEUMATOLOGY
11:00:00:00 OBSTETRICS & GYNECOLOGY
12:00:00:00 OPHTHALMOLOGY
13:00:00:00 RESPIRATORY, ALLERGY, COUGH & COLD
14:00:00:00 UROLOGICALS
15:00:00:00 VITAMINS, HEMATINICS & ELECTROLYTES
16:00:00:00 DIAGNOSTICS & MISCELLANEOUS AGENTS

FRS - [DB0PFCT0] - [TREEVIEW (FORMULID=35)]

FILE  MAINTENANCE  REPORTS  HELP

SAVE | CLEAR ALL | EXIT | DISPLAY MODE [TREE VIEW ONLY ▼] | HIDE BLOCK ATTRIBUTES | ✚

FORMULARY BLOCKS                                    FORMULARY FLAGS

- 01:00:00:00 ANTI INFECTIVES
- 02:00:00:00 ANTINEOPLASTIC 7 IMMUNOSUPPRESSANT DRUGS
- 03:00:00:00 AUTONOMIC & CNS DRUGS, NEUROLOGY & PSYCH
  - ☑ 03:01:00:00 NARCOTIC ANALGESICS
  - ☑ 03:02:00:00 PROPOXYPHENE
  - ☑ 03:03:00:00 NON-NARCOTIC ANALGESICS
    - ☑ 03:03:01:01 NSAIDS
    - ☑ 03:03:01:02 NSAIDS-SPECIFIC COX-II INHIBITORS
      - CHEMICALS
        - ☑ 18979 CELECOXIB
        - ☑ 20208 ROFECOXIB
          - TRADE NAMES
            - ☑ 30020 VIOXX  ← 154
              - DOSAGE FORMS
                - ☑ 082 SUSPENSION, ORAL (FINAL DOSE FORM)
                - ☑ 600 TABLET
                  - STRENGTHS
                    - ☑ 0255 12.5MG
                    - ☑ 0320 25MG
                    - ☑ 0390 50MG
  - ☑ 03:03:02:00 SALICYLATES
  - ☑ 03:03:03:00 MISCELLANEOUS ANALGESICS
  - ☑ 03:03:05:00 NARCOTIC ANTAGONISTS
  - ☑ 03:04:00:00 MIGRAINE & CLUSTER HEADACHE THERAPY
  - ☑ 03:05:00:00 ANTIPARKINSONISM AGENTS
  - ☑ 03:06:00:00 ANTICONVULSANTS
  - ☑ 03:07:00:00 MISCELLANEOUS NEUROLOGICAL THERAPY
  - ☑ 03:08:00:00 MUSCLE RELAXANTS & ANTISPASMODIC THERAPY 152A, 152B

FRS - [DB0PFCT0]
FILE   MAINTENANCE   REPORTS   HELP

STANDARD FORMULARY SETUP WIZARD-STEP 4 OF 6

160 — PLEASE SET EACH DOSAGE FORM STATUS FOR EITHER YES OR NO.   162   164

DOSAGE FORM RULE(S).

| NAME: | DESCRIPTION: | YES/NO |
|---|---|---|
| DOSAGE FORM RULE 1 | AEROSOLS - LINGUAL | YES |
| DOSAGE FORM RULE 2 | AEROSOLS - NASAL | YES |
| DOSAGE FORM RULE 3 | AEROSOLS - INHALATION (MDIs) | YES |
| DOSAGE FORM RULE 4 | COMPOUNDING PRODUCTS | YES |
| DOSAGE FORM RULE 5 | IMPLANT | NO |
| DOSAGE FORM RULE 6 | INHALANT - POWDER | YES |
| DOSAGE FORM RULE 7 | INHALANT - SOLUTION | YES |
| DOSAGE FORM RULE 8 | INTRAUTERINE SYSTEM | NO |
| DOSAGE FORM RULE 9 | IRRIGATION | NO |
| DOSAGE FORM RULE 10 | LARGE VOLUME PARENTERAL | NO |
| DOSAGE FORM RULE 11 | TOPICAL MOUTH & THROAT | YES |
| DOSAGE FORM RULE 12 | OCULAR SYSTEMS | YES |
| DOSAGE FORM RULE 13 | OPHTHALMIC PREPARATIONS | YES |

<< PREVIOUS     NEXT >>     CLOSE

APPARATUS AND METHOD FOR CONSTRUCTING FORMULARIES

RELATED APPLICATION

This application claims the priority of U.S. Provisional Application No. 60/349,407 filed Jan. 22, 2002, which is incorporated herein by reference.

BACKGROUND OF THE INVENTION

1. Technical Field

The present invention relates to prescription benefits and, more particularly to an apparatus and method for creating, modifying, and maintaining formularies that define prescription drugs and treatments supported by prescription benefit programs.

2. Description of the Related Art

Employers often provide employees with various benefits upon commencing their employment. These benefits typically include a package which covers healthcare and prescription drugs (or products). The healthcare package is generally provided through a healthcare provider. The specific coverage offered to an employee can depend on several factors, including the particular coverage program negotiated by the employer. For example, the benefits available can be different depending on the medical coverage desired, the prescription medication available, etc. Furthermore, the specific benefits requested will directly effect the coverage cost.

Regardless of the coverage, the healthcare provider will place certain restrictions and/or limitations on the prescription medication, or drugs, an employee can take. These restrictions determine whether the healthcare provider will cover the cost of a prescription in full or in part. For example, the healthcare provider may deny coverage for a name brand prescription product, while defining different levels of copay for various generic or substitute products. Healthcare providers use formularies to define the prescriptions products and treatments that a particular plan will cover. A formulary is a comprehensive list of pharmaceutical products that can be used as preferred products within a prescription plan offered to an employer. The formulary can include both brand name and generic products. The specific products in a formulary are selected, in part, based on safety, efficacy, and cost. Formularies can also be used, in part, to define the hierarchies that determine the various levels of copay that the healthcare provider will cover.

Design of a new formulary typically requires review of hundreds and sometimes thousands of individual prescription (e.g., pharmaceutical) products based on assigned National Drug Code (NDC) identifiers. As used herein, the term pharmaceutical product refers to any product, treatment, and/or therapy that is assigned a National Drug Code identifier. Each prescription coverage plan offered by the healthcare provider can include hundreds and sometimes thousands of different products. The healthcare provider must also define rules that determine how newly approved products will be treated under a particular formulary. As can be seen, the design and implementation of formularies for prescription coverage programs can involve numerous and complex decision-making steps resulting in the consumption of a great deal of time. Adding to this complication is the fact that a healthcare provider has many clients, each of whom may request different prescription coverage plans.

Various difficulties have been encountered in creating and modifying formularies. One process, originally practiced by the current assignee, has involved extensive dialogue and/or interaction with healthcare providers for creating and modifying the formulary for each prescription coverage plan. This process has proved very time consuming and complex due, at least in part, to the large number of products under government regulation. Specifically, there are over 140,000 products assigned NDC identifiers that may require individual review by the healthcare provider.

Traditionally, the healthcare provider would meet with a clinical account executive (CAE) to discuss the general requirements of the prescription coverage plan. The essence of the discussion, or the discussion itself, would be captured and converted to a computer document. The document would then be reviewed by formulary operations personnel, or programmers, to determine if it contains sufficient information to create the formulary. The programmers compare information contained in the document with clinical information contained in an Integrated Drug File (IDF) to determine which name brand products, generics, etc. should be included in the formulary for the prescription coverage plan. This results in the creation of a temporary formulary that is repeatedly exchanged between CAEs and programmers for review and modification.

Once the CAE is satisfied with the temporary formulary, it must be reviewed with the healthcare provider. This process again must be repeated until the healthcare provider is satisfied. The dialogue between different parties can often extend for weeks and months to create and/or modify the formulary for a single prescription coverage plan. Additionally, the information must be presented on paper, or other tangible form, for review and modification by the healthcare provider. For example, the NDC identifiers of all products in the prescription coverage plan must be reviewed and marked for inclusion or exclusion in the formulary. Thus, data accuracy can often become an issue.

Maintaining and modifying formularies to accommodate client needs can often prove to be a challenging task requiring many months to complete. In addition, inherent error potentials cannot be eliminated. Furthermore, these errors will often translate directly to increased costs as well as exposure to liability for the healthcare provider. Over time, these costs can quickly accumulate, particularly when formularies require an extended period of time to create.

Accordingly, there exists a need for a system capable of quickly and efficiently creating prescription formularies.

There also exists a need for a system which minimizes the amount of time required to create a formulary while providing access to all products assigned on NDC identifier.

There exists a further need for a system which allows healthcare providers an ability to create formulary templates that can be quickly modified to suit client needs.

There exists a still further need for a system capable of automatically incorporating newly approved products into an existing formulary.

SUMMARY OF THE INVENTION

It is therefore one feature and advantage of the present invention to address at least some of the shortcomings of the prior art in constructing prescription formularies.

It is another optional feature and advantage of the present invention to provide a system capable of quickly an efficiently creating prescription formularies.

It is yet another optional feature and advantage of the present invention to provide a system which minimizes the amount of time required to create a formulary while providing access to all products assigned an NDC identifier.

It is a further optional feature and advantage of the present invention to provide a system which allows healthcare providers an ability to create formulary templates that can be quickly modified to suit client needs.

It is a still further optional feature and advantage of the present invention to provide a system capable of automatically incorporating newly approved products into an existing formulary.

The foregoing, and various other needs, are addressed, at least in part, by the present invention, wherein pharmaceutical products assigned NDC identifiers are sorted into predefined categories and subcategories based on predetermined relational characteristics such that groups of related products can be either simultaneously or individually selected for inclusion in the formulary.

According to one aspect of the invention, a method of constructing a formulary comprises the steps: compiling a list of pharmaceutical products; sorting the pharmaceutical products into at least one category based on predetermined relational characteristics; and selecting a plurality of pharmaceutical products from the at least one category, the selected pharmaceutical products to be supported by the formulary. Such a method allows healthcare providers to quickly and efficiently construct formularies. Healthcare providers are also capable of offering a greater number of prescription plans to better suit patient needs.

One optional embodiment of the invention defines sixteen categories for classifying the pharmaceutical products. The categories are defined based on certain characteristics or similarities between the pharmaceutical products. The categories can optionally be selected such that they encompass all, or substantially all, the pharmaceutical products that have been assigned NDC identifiers. Another optional embodiment of the invention conducts routine retrieval of information on newly-released pharmaceutical products. The newly released pharmaceutical products are then classified into the product categories. Optionally, the newly released products can be automatically included into existing formularies based on requirements of the healthcare provider.

According to another aspect of the invention, a method of remotely establishing requirements for implementing a formulary, comprises the steps: accessing, over an electronic network, a computer system containing pharmaceutical products sorted into at least one category based on predetermined relational links; and selecting a plurality of pharmaceutical products to be supported by the formulary. Such a method advantageously allows healthcare providers to conveniently design and review formularies independently of a prescription coverage provider.

According to another aspect of the present invention, a method of implementing a formulary for processing prescription claims, comprises the steps: compiling a list of pharmaceutical products; sorting the pharmaceutical products into at least one category based on predetermined relational characteristics; providing access to a computer system containing formulary information to a user; and receiving selections of pharmaceutical products to be supported by the formulary from the user.

According to another aspect of the present invention, a method of implementing a formulary comprises the steps: compiling a list of pharmaceutical products; sorting the pharmaceutical products into at least one category based on predetermined relational characteristics; selecting a plurality of pharmaceutical products from the at least one category, the selected pharmaceutical products to be supported by the formulary; receiving a prescription claim for coverage of a prescribed pharmaceutical product; accepting coverage for the prescription claim based on whether the prescribed pharmaceutical product is supported by the formulary; and rejecting coverage for the prescription claim based on whether the prescribed pharmaceutical product is not supported by the formulary. According to such a method, healthcare providers are capable of offering multiple prescription plans to patients. Additionally, prescription coverage providers can quickly and efficiently process prescriptions.

According to an optional embodiment of the present invention, various data is collected while processing prescriptions. The data can then be used to prepare a budget analysis for the costs associated with implementing the formulary. The healthcare provider can use this information to determine whether changes should be made to the formulary in order to better accommodate patients.

Other aspects of the invention provide a system for constructing formularies. The system includes a central computer, at least one additional computer, and a communication interface. The communication interface is used to establish a communication channel between the central computer and the additional computers. The central computer compiles a list of pharmaceutical products and sorts them into various categories based on predetermined relational characteristics and/or similarities. The additional computers can be used to select pharmaceutical products that will be supported by the formulary.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

FIG. 8 is an illustration of a formulary setup menu according to an exemplary embodiment of the present invention;

FIG. 9 is an illustration of a sample category listing according to an exemplary embodiment of the present invention;

FIG. 10 is an illustration of the hierarchy structure of the categories;

FIG. 11 is an illustration of a sample menu for defining inclusion rules;

FIG. 12 is an illustration of a sample menu for defining delivery limitations.

DETAILED DESCRIPTION OF THE INVENTION

Figure 1:
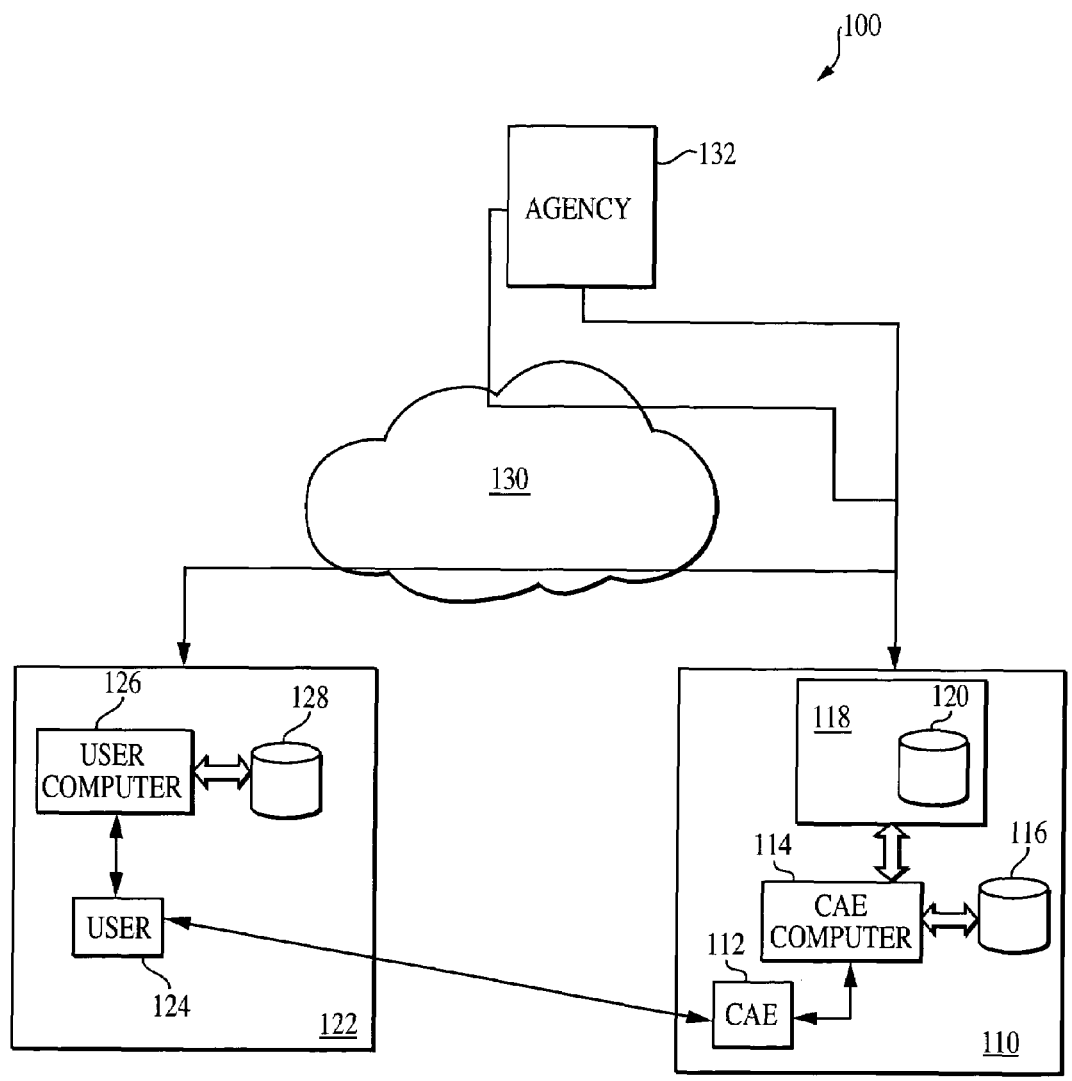
FIG. 1 is a block diagram illustrating an arrangement for managing formularies.

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Prior to describing the details of the invention, a brief discussion of some of the notations and nomenclature used in the description will be presented. Next, a description of exemplary hardware useable in practicing the invention will be presented.

Notations and Nomenclature

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are preferably machine operations, although the operations may also be manual in alternative embodiments. Useful machines for performing the operation of the present invention include general purpose digital computers or similar devices.

The present invention also relates to apparatus for performing these operations. This apparatus may be specially constructed for the required purpose or it may include a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

Formulary Management System

Turning now to the drawings and initially to FIG. 1, a system is shown for managing formularies according to an exemplary embodiment of the present invention. The formulary management system 100 includes a prescription coverage provider 110, a healthcare provider 122, and an official agency 132. The prescription coverage provider 110 can be, for example, a large pharmaceutical dispensing company responsible for filling prescription claims for the healthcare provider 122 in accordance with predefined formularies. The prescription coverage provider 110 includes at least a clinical account executive (CAE) 112 and a central computer system 118. The CAE 112 has access to a local computer, such as a personal computer or laptop 114 that can include internal or external data storage devices 116. The CAE computer 114 is capable of storing and retrieving information and/or records from the external storage device 116. In addition, the CAE computer 114 is operatively coupled to the central computer system 118. More particularly, the CAE computer 114 can be part of a network system which interconnects multiple computers with each other and with the central computer system 118. Such connections can include, for example, local area networks (LAN), wide area networks (WAN), direct dial networks (e.g., modem to modem connections), public networks (e.g., the Internet), World Wide Web, etc. As illustrated in FIG. 1, the central computer system 118 also includes an external storage device 120 which can optionally be in the form of a database server.

Accordingly, the CAE 112 is capable of using the CAE computer 114 to access the central computer 118 and exchange information from various locations. Furthermore, data retrieved from the central computer 118 can be temporally and/or permanently stored on the external storage device 116. Likewise, data can be retrieved by CAE computer 114 and transmitted to the central computer system 118. It should be noted that although only one CAE 112 and associated CAE computer 114 is illustrated in FIG. 1, the present invention can provide support for multiple CAE's simultaneously accessing the central computer system 118 and interacting with the central computer system 118 as well as other CAEs. Thus, the present invention should not be restricted to a single CAE 112.

The healthcare provider 122 includes a user 124, such as an account representative or manager, capable of accessing a user computer 126. As illustrated in FIG. 1, the user computer 126 can also be coupled to an external data storage device 128. The user 124 is responsible for representing the healthcare provider 122 and identifying specific formulary needs to the CAE 112. The healthcare provider 122 (or user 124) is capable of establishing a connection with the prescription coverage provider 110 over an electronic network 130. Such a connection can typically be established between the user computer system 126 and the central computer 118 of the prescription coverage provider 110. Such a connection would typically take place across an electronic network 130 as depicted in FIG. 1. The electronic network 130 can be a public network such as the Internet or World Wide Web. Alternatively, the electronic network 130 can be a private network using private connection lines and/or conventional modems to establish a connection with the prescription coverage provider 110. Regardless of the type of network used to establish a connection, various types of protocols can be used for exchanging data between users such as, TCP/IP, html, FTP, etc. It is also possible for the CAE 112 to meet directly, or in person, with the user 124 (e.g., healthcare provider representative).

The central computer 118 of the prescription coverage provider 110 stores information pertaining to prescription products that can used in the formulary. The prescription products are typically drugs and/or controlled substances that are useable for medicinal purposes and/or treatments. Such products are assigned specific identifiers known as a National Drug Code (NDC) identifier. New products entering the market from pharmaceutical companies must obtain government (or official) approval prior to introduction to the public. As part of this approval process, a unique NDC identifier is assigned to the pharmaceutical product. Accordingly, every pharmaceutical product that must be obtained by prescription has a unique NDC identifier. As previously indicated, the term pharmaceutical product (or product) is used to refer to any product, treatment, and/or therapy having an assigned NDC identifier. Currently, there are over 140,000 products assigned NDC identifiers.

As new products are introduced to the public, they may become available for coverage by a given formulary. It is therefore necessary to constantly update and maintain the information stored by the central computer system 118. This can be accomplished, at least in part, through data exchange with the Government agency 132. More particularly data pertaining to newly released products can be used to supplement and/or update the records of the central computer system 118. According to one embodiment of the present invention, the central computer system 118 contacts the government agency 132 on a periodic, but regular, basis in order to determine if any new pharmaceutical products have been approved for public use. If new products have been approved, then a request is made to the government agency 132 to obtain information pertaining to the newly released product. This information can include, for example, the NDC identifier, the approved dosages, the available delivery methods, etc. As illustrated in FIG. 1, the connection between the government agency 132 and the central computer system 118 can be established across the exemplary electronic network 130. Alternatively, a direct connection outside of the network can be used to access information from the government agency 132. As previously indicated, such a direct connection can be made using a modem to modem connection, a private network connection, etc.

According to an optional embodiment of the present invention, newly released products can be automatically added to a healthcare provider's formularies. This can be accomplished, for example, by first reviewing the category (or subcategory) in which a newly released product has been classified. If the healthcare provider 122 has exceeded a threshold value of products in the category for coverage, then the newly released product would be added to the formulary. The threshold value can be a number or percentage. For example, if a healthcare provider 122 has selected more than 50% of the products in a category, there is a great likelihood that they would be interested in supporting the newly released product. Additional factors can optionally be considered. A healthcare provider 122 that has declined to include coverage of expensive products where alternatives are available, would likely reject coverage of a newly released product that has a high cost if alternatives are available. Thus, a newly released product which costs more, or significantly more, than available products would not be automatically included in the formulary. Furthermore, the healthcare representative 124 can provide specific requests, in the form of notes, which indicate the criteria for adding newly released products. In such a situation, the notes entered during creation of a formulary would be reviewed to determine whether newly released products should be incorporated into the formulary.

Formulary Construction

Figure 2:
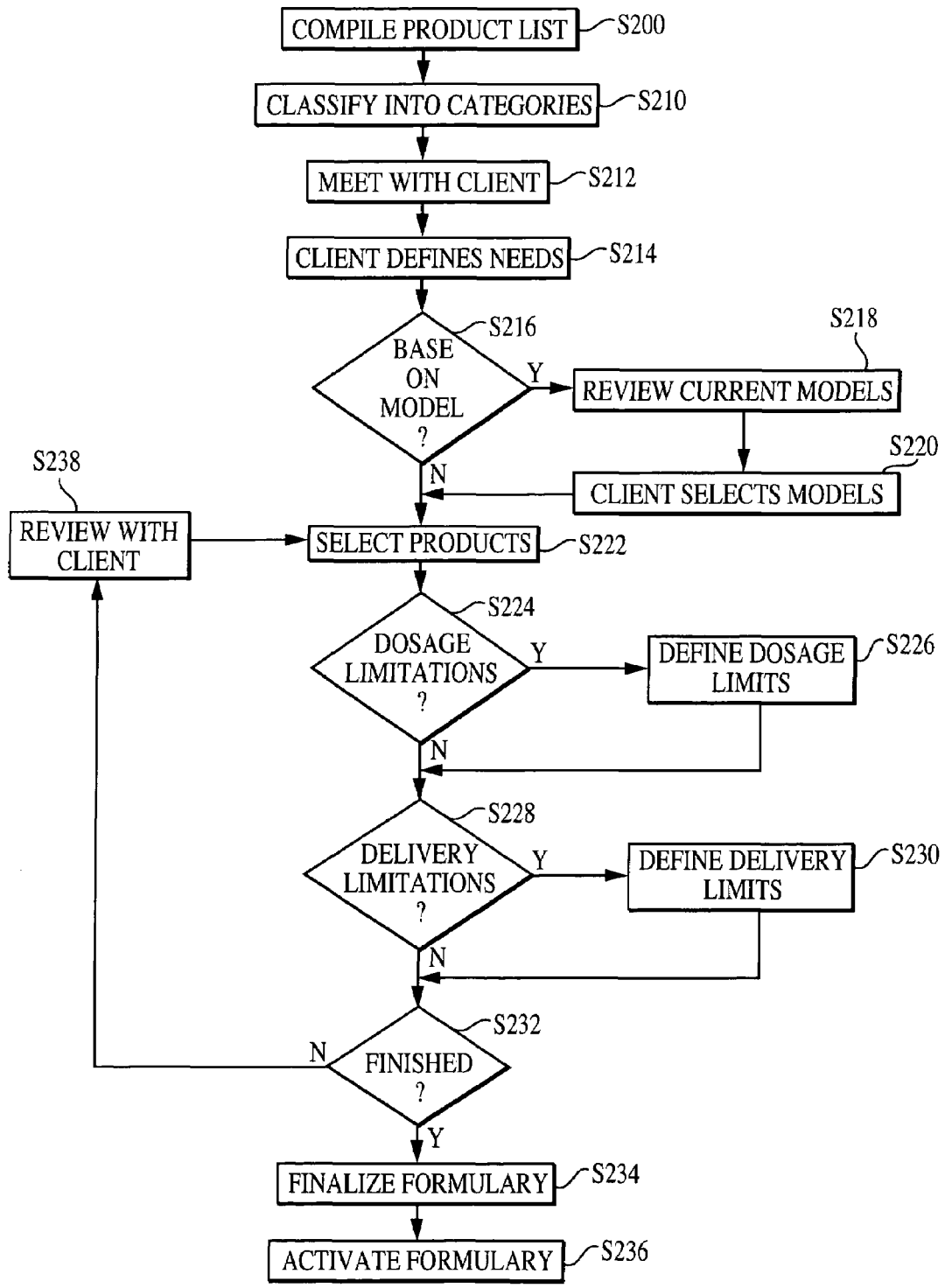
FIG. 2 is a flow chart outlining the steps performed to construct a formulary.

Turning now to FIG. 2, the steps for constructing a formulary will now be described. At step S200, a list of products available for coverage is compiled. The list consists of all available products that have an assigned NDC identifier. In addition, as new products are released, the central computer system 118 retrieves updated information from the official agency 132 and includes those products when compiling the list. At step S210, the products are classified into various categories. The categories correspond to particular relational characteristics that are shared by different products. According to an exemplary embodiment of the present invention, the products are classified into sixteen categories. The sixteen categories are defined as therapeutic chapters or product types. In addition, the categories can be optionally organized in a tree structure such that they contain subcategories which contain further subcategories, etc.

The sixteen categories are selected such that they encompass all existing drugs, chemicals, agents, etc., that are currently available for use by patients. The categories can be optionally organized to encompass only the products (drugs, chemicals, agents, etc.) most frequently used. For example, one category can be designated anti-infectives. This category would be designed to contain all products available for combating infections. Navigating through the anti-infective category would lead to different types/families of anti-infectives such as, anti-virals, penicillins, tetracyclines, etc. Subsequent navigation through the penicillins, for example, would lead to specific products that can be taken to combat various infections. Thus, depending on the specific implementation, a very high level of granularity can be achieved while simultaneously grouping products into various levels of similarity.

At step S212 a meeting is established between the CAE 112 and the healthcare representative, or user, 124. The meeting can be conducted in person, or alternatively, a connection can be established between the healthcare representative 124 and the CAE 112 over the electronic network 130. The healthcare representative 124 can also conduct the meeting using a conventional telephone. At step S214, the healthcare representative 124 defines the general type of formulary coverage being sought. For example, this discussion would entail the amount of products to be covered under the formulary and the associated costs that would be passed on to the patient.

At step S216, it is determined whether the healthcare representative 124 would like to base the desired formulary on a formulary model that has been previously prepared by the prescription coverage provider 110. More particularly, prior to, and after, meeting with healthcare representatives 124, the prescription coverage provider 110 can construct model formularies covering a majority of products desired by various healthcare providers. For example, the model formularies can be constructed to represent a low cost product coverage, a medium cost coverage, and a high cost product coverage. While each plan could provide similar product coverage, the difference in cost may stem from coverage of name brand medication as opposed the generic brand. Additionally, certain types of unapproved products and/or treatments methods may not be covered by the formulary. Accordingly, the healthcare representative 124 would be provided with a summary or description of the type of coverage available from the different model formularies in order to determine if they would like to simply incorporate one of the model formularies or modify one of the model formularies to better suit their needs.

If the healthcare representative 124 would like to base the current formulary on a model, then control passes to step S218. The healthcare representative 124 would review the available model formularies together with a description of their coverage-type. At step S220, the healthcare representative 124 selects a model formulary from which to base the current formulary. Control then passes to step S222. If the healthcare representative 124 does not want to base the current formulary on a model, control would also pass to step S222. At step S222, the healthcare representative 124 would identify the products they would like to cover with the current formulary. In addition, if the healthcare representative had selected a model formulary and would like to modify it by incorporating additional products they would also select these products at step S222.

At step S224, it is determined if the healthcare representative 124 would like to set limitations on the dosage for specific or groups of products. Such dosage limitations can correspond to, for example, the strength of the product per dose, the release time (e.g., extended release), etc. This corresponds to a situation where the healthcare provider 122 wishes to support a particular product at regular dosage strengths that provide the same benefits as the extended dosage strengths, but minimizes the cost to patients.

If the healthcare representative 124 would like to provide dosage limitations, control passes to step S226. The different dosage options are reviewed by the CAE 112 and the healthcare provider 124 decides which dosage options the formulary should cover. Control then returns to step S228. If the healthcare representative 124 does not wish to provide dosage limitations, control also passes to step S228. It is then determined if the healthcare representative 124 would like to incorporate limitations on the manner in which the product is delivered to patient. The delivery method corresponds to the form of the product such as, for example, oral, nasal, inhalant, topical, injection, etc. If the healthcare representative 124 would like to include delivery limitations, control passes to step S230. The different types of delivery methods for the products are discussed with the CAE 112. Based on this discussion, the healthcare representative 124 identifies which products will incorporate limitations on the delivery method. For example, the healthcare representative 124 may wish to limit the use of an inhalant, in situations where a tablet or capsule is available. Once the delivery limits are identified, or if no delivery limitations will be incorporated, control passes to step S232. Alternatively, control would also pass to step S232 if no limitations would be placed at step S228.

At step S232 it is determined if the healthcare representative 124 is satisfied with the content and coverage of the current formulary. If the healthcare provider 124 is satisfied, then control passes to step S234 where the formulary is finalized. This can be done subsequent to the meeting with the healthcare representative 124. In other words, once all of the requirements of the healthcare representative 124 have described and incorporated into the formulary, the CAE 112 will review the information and make the necessary modifications to ensure that the client's needs are met. At step S236, the formulary is activated and prescription claims can be received and processed. If the healthcare representative 124 is not satisfied with the content of the formulary, however, then control passes to step S238 where the contents of the formulary can be reviewed. Optionally, control can return to step S222 where additional products can be selected and incorporated into the formulary.

During the meeting with the healthcare representative 124, the CAE 112 will often incorporate notes reflecting the thoughts and/or reasons for including or excluding certain products. These notes can be used, in part, to subsequently determine whether, or how, newly released products will be incorporated into the formulary. For example, a healthcare representative 124 may indicate the formulary should not cover the cost of extended release medications where a normal release version is currently available. Accordingly, if any extended release product is received by the central computer system 118, coverage would be automatically denied when the formulary is activated. The notes entered by the CAE 112 are also carried to different computer screens throughout various stages of the meeting. More particularly, as the notes are entered in the CAE computer 114, the data is saved and easily accessible in an organized fashion so that all the notes can easily accessed and reviewed simultaneously. There is no need to navigate to a section containing a product, or family of products, where the note was initially entered.

Figure 3:
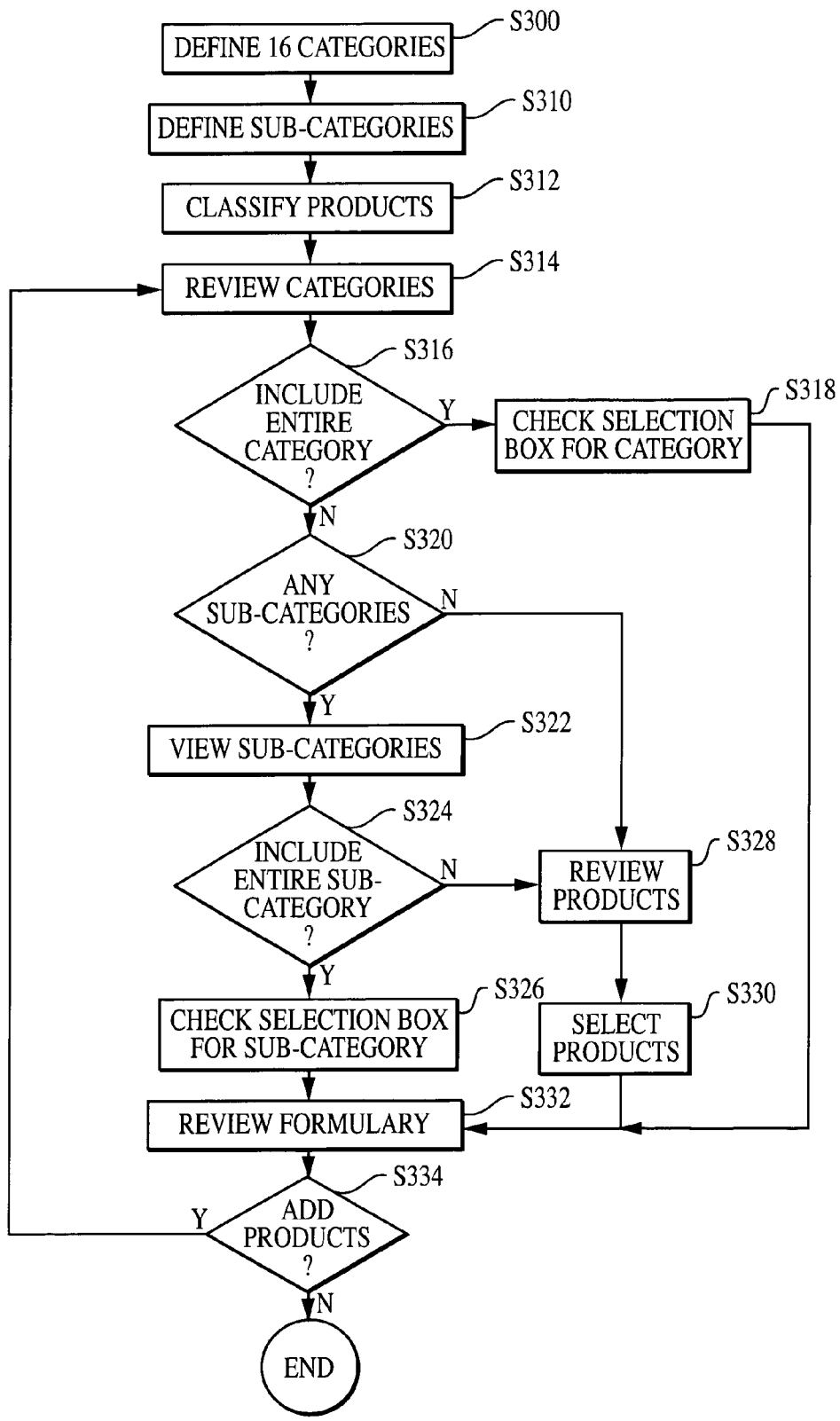
FIG. 3 is a flow chart detailing the steps performed to select products for coverage by the formulary.

With reference to FIG. 3, an exemplary embodiment for selecting products to be covered by the formulary will now be described. At step S300, sixteen different categories are defined for the products. At step S310 various subcategories are defined for each of the sixteen categories. As previously indicated, the number of categories and subcategories used can optionally depend on the specific manner that the prescription coverage provider would like to organize the products. Accordingly, there can be varying numbers of categories and subcategories depending on the requirements of a particular healthcare provider. At step S312, the products are classified into the different categories and subcategories.

At step S314, the healthcare representative 124 reviews each of the top level (e.g., sixteen) categories to determine their contents. At step S316, it is determined whether the healthcare provider 122 would like the formulary to cover the entire contents of a category being reviewed. More particularly, the healthcare representative 124 decides if all the products contained within the selected category, and subsequent subcategories, should be covered by the formulary. If the entire category of products will be covered, then the healthcare representative 124 makes a selection at step S318. According to an exemplary embodiment of the invention, selection of the entire category can be accomplished by utilizing a cursor control device, such as a mouse or stylus, to make a graphical selection of the category. The selection can be in the form of a check box or a radio button that is selected by the cursor control device to convey the healthcare representatives choice. Alternatively and/or optionally, an input device such as a keyboard can be used to make the selection. Upon selecting the entire category, control passes to step S332.

If the healthcare representative 124 does not wish to include the entire category of products, control passes to step S320. It is then determined if there are any subcategories contained within the selected category. If there are additional subcategories, then at step S322, the healthcare representative 124 reviews each of the subcategories. At step S324 it is determined if the entire subcategory of products being reviewed should be included, or covered, by the formulary. If the entire subcategory will be included, then control passes to step S326 where the healthcare representative 124 would, for example, check the selection box for the subcategory. If the entire subcategory will not be covered by the formulary or if there were no subcategories found at step S316, then control passes to step S328. The healthcare representative 124 reviews the products listed in either the category, subcategory, subsequent subcategory, etc. As the products are reviewed, they can be individually checked (e.g., selected) for coverage by the formulary. This is done at step S330.

It should be appreciated that the process of reviewing subcategories may need to be repeated multiple times before arriving at a point where individual products can be reviewed. This is a direct result of the nested/tree structure used to arrange and categorize the products. Consequently, a different organizational structure and/or product category definitions can alter the exact sequence for reviewing the subcategories and products. At step S332, the healthcare representative 124 reviews the formulary, or rather, the products covered by the formulary. At step S334, it is determined whether the healthcare representative 124 would like to add additional products to be covered by the formulary. If additional products will be added, then control passes to step S314. At this point, the healthcare representative 124 reviews the categories, as previously described, and selects additional products to be covered. If no additional products will be included, then the process ends.

Figure 4:
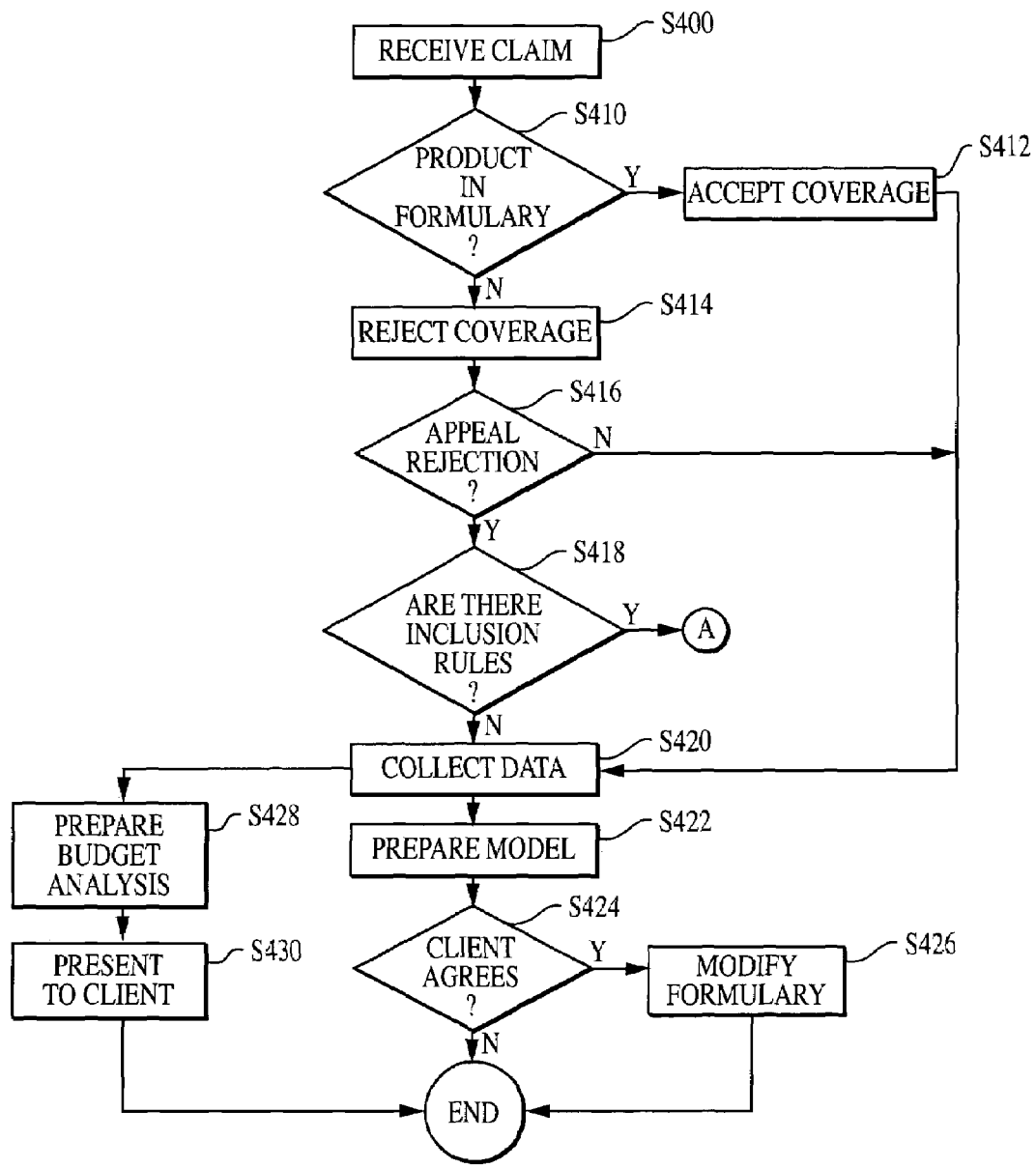
FIG. 4 is a flow chart detailing the steps performed to process prescription claims for products.

Turning to FIG. 4, a flowchart is shown for illustrating the manner in which claims are processed under an active formulary. At step S400, the claim is received by the prescription coverage provider. This corresponds to a situation where a patient has received a prescription from a physician and desires to fill the prescription. The patient would take the prescription form to a pharmacy where the product would be received and dispensed by a pharmacist. Depending on the type of healthcare coverage the patient has, the cost of filling the prescription may vary. In order to determine the cost, the pharmacist will, in part, submit a claim to the prescription coverage provider 110 for covering the cost of the prescribed product. Depending on the cost covered by the prescription coverage provider and the total cost of the product, the patient could optionally be charged a residual value, e.g., a copay.

Upon receiving the claim, it is determined if the product is in the formulary, or covered by the formulary. If the product is covered by the formulary, then coverage is accepted at step S412. Control then passes to step S420. If the product is not covered by the formulary then coverage for the product is rejected. At step S416, the patient may optionally have an opportunity to appeal the rejection for coverage. This particular step may not be immediately performed by the patient. More particularly it may require a formal submission of an appeal to the healthcare provider 122 in order to initiate the process. If the patient will not appeal the rejection, then control passes to step S420. If the patient would like to appeal the rejection, then at step S418 it is determined if there are any inclusion rules for the product being rejected for coverage. The inclusion rules correspond to alternatives that the healthcare provider 122 has specified, or special circumstances that the healthcare provider 122 would allow, in order to provide coverage for a non-formulary product. If there are inclusion rules, control passes to Block A (described in more detail below with reference to FIG. 5). If there are no inclusion rules, then there are no previsions or special circumstances for providing coverage for the product. The claim rejection would stand.

As claims are received and processed by the prescription coverage provider 110, various data is collected. This is illustrated at step S420. The data can be used for various reasons such as providing better formulary coverage for products, providing the healthcare provider with statistical information regarding formulary coverage, preparing model formularies, etc. For example, at step S422, a model formulary can optionally be prepared based on the data collected. The model formulary can be presented to the healthcare provider 122 at step S124 to see if they would like to accept it as an on-going formulary. If the healthcare provider 122 agrees to utilize the model formulary, then control passes to step S426. The healthcare provider's formulary is modified based on the variations presented in the model formulary. The process is then terminated. Alternatively, if the healthcare provider 122 does not wish to accept the model formulary, the process would also end.

As another example, the data collected at step S420 can be used to provide beneficial information to the healthcare provider 122. At step S428, for example, a budget analysis can optionally be prepared based on the costs incurred for covering various products under the formulary. The costs incurred can be based on normal formulary coverage, non-formulary coverage, and/or appealing rejected claims. At step S430, the budget analysis can be presented to the client for review. The budget analysis can be used, in part, to assist the client in providing optimum coverage to patients at the lowest possible cost.

Figure 5:
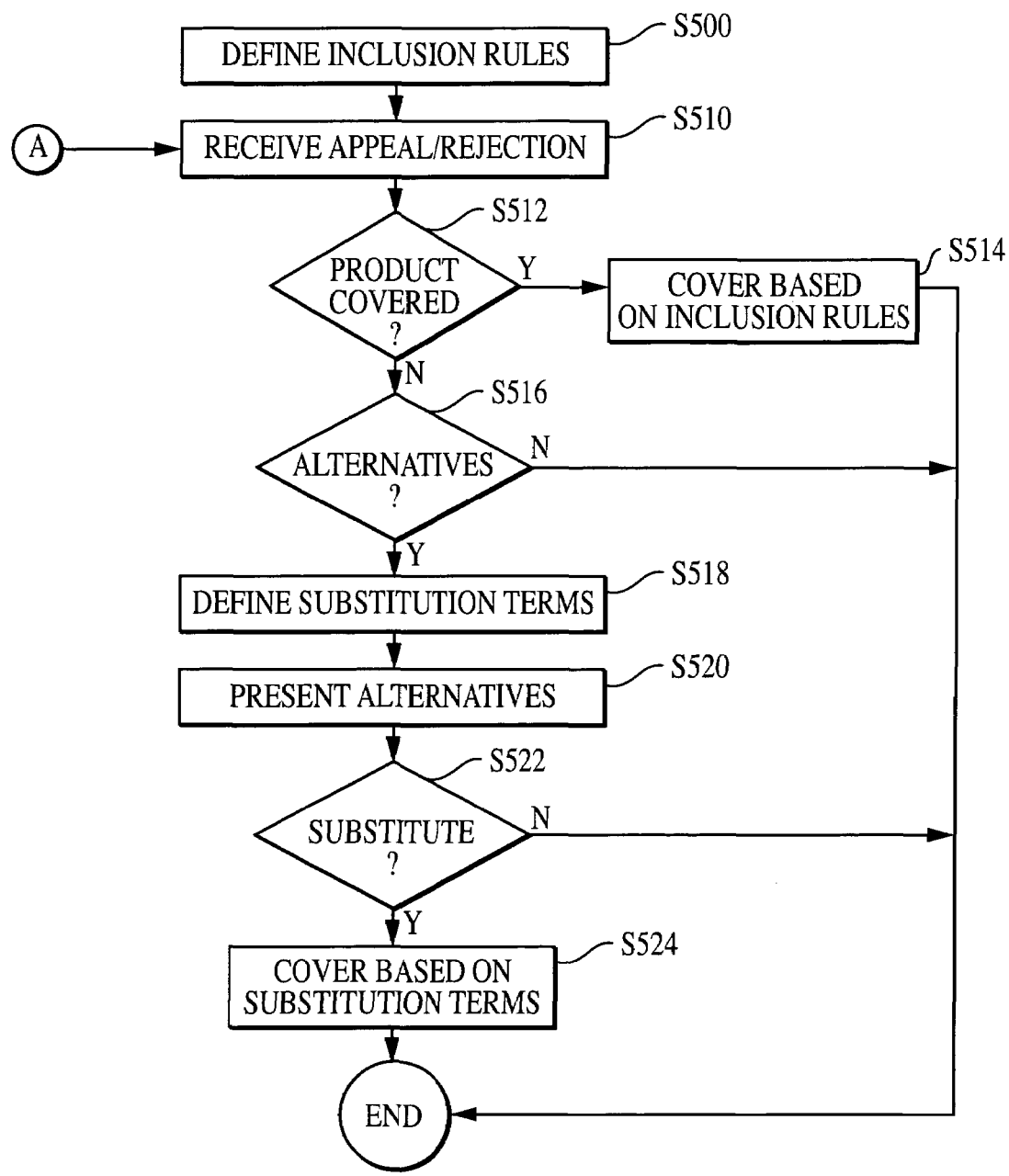
FIG. 5 is a flow chart outlining alternatives available for product not covered by the formulary.

FIG. 5 illustrates additional details for processing an appeal according to an exemplary embodiment of the invention. As previously discussed, unless there are exclusion rules, an appeal will typically be rejected. At step S500, various inclusion rules for processing appeals are defined. This corresponds to a point when the healthcare representative 124 is defining the type of coverage that will be provided by the formulary. The inclusion rules can be incorporated as part of the notes entered by the CAE 112, or they can be entered into a separate section designated for inclusion rules. At step S510, an appeal for a rejected claim coverage is received by the prescription coverage provider 110. At step S512, it is determined if the inclusion rules cover the product that has been rejected. If there is an inclusion rule to cover the rejected product, then control passes to step S514. At step S514, the product coverage is approved based on the inclusion rule provided.

The inclusion rules can include, for example, a higher copay amount that must be paid by the patient in order to support coverage of a non-formulary product. The inclusion rules can also define certain limitations on dosage, name brand, etc. that will be covered. If there are no inclusion rules to cover the rejected product, then at step S516 it is determined if there are any alternatives that would provide similar benefits as the rejected product. For example, consider a rejected product which is a name brand antibiotic. An alternative could optionally be a generic brand antibiotic, have the same, or substantially similar, active chemical ingredient. If there are no alternatives available then the appeal process terminates and the claim rejection stands. If there are alternatives, then the terms of substituting the alternative are presented to the patient based on predetermined conditions defined by the healthcare representative 124. The substitution terms can include, for example, the requirement of a generic brand as opposed to name brand product. In addition, the substitution terms can be defined based on notes taken by the CAE 112 during the meeting with the healthcare representative 124 or they can be defined directly by the healthcare representative 124.

At step S520, the alternatives are presented to the patient. If the patient is willing to accept the substitute product, then control passes the step S524 where the substituted product is covered and dispensed to the patient based on the substitution terms previously defined. The process would then end. If, however, the patient would not like to accept the substitute product, then the process would end and the claim rejection would stand.

Figure 6:
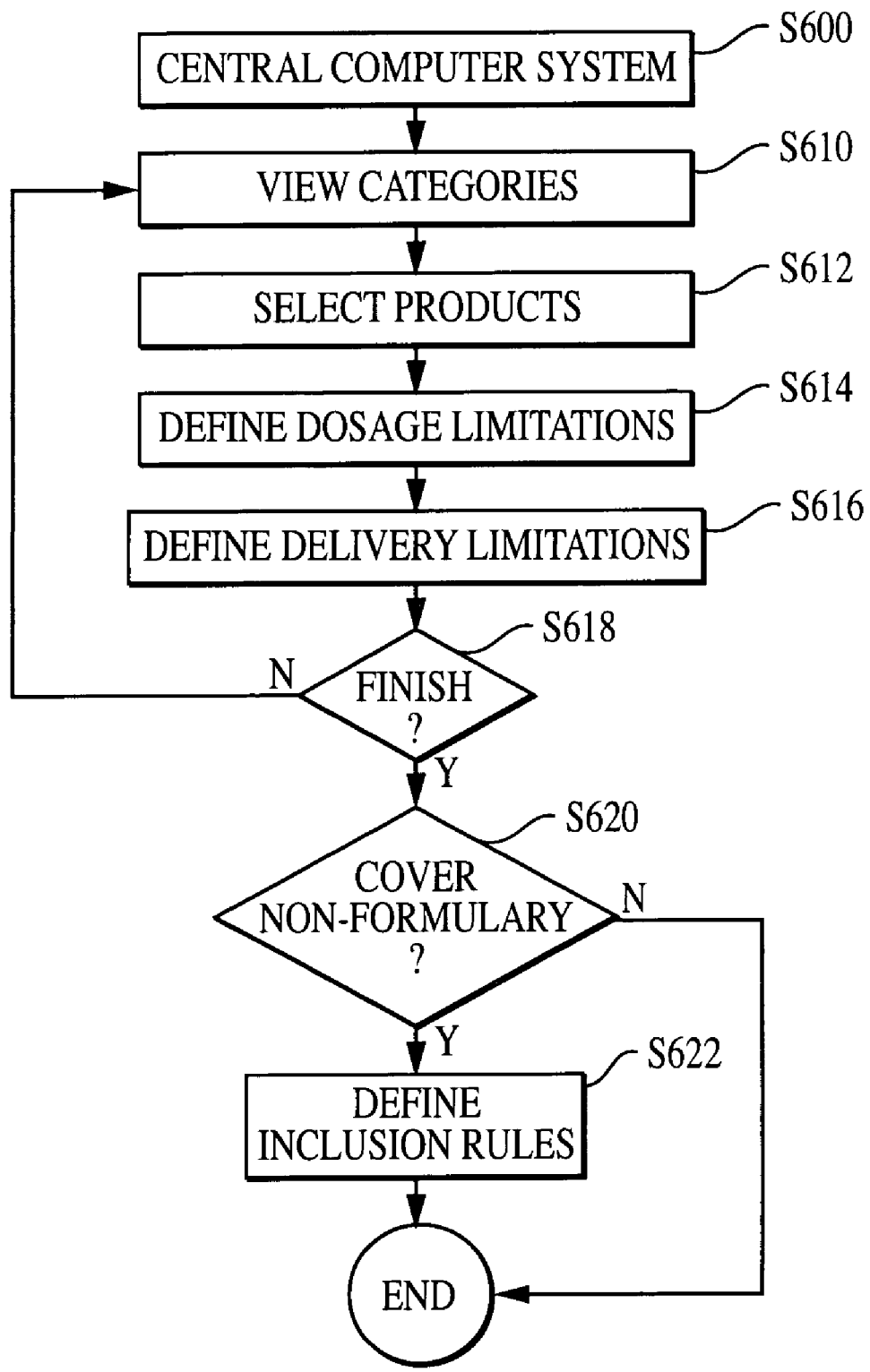
FIG. 6 is a flow chart outlining the steps performed by a user to construct a formulary.

FIG. 6 illustrates the steps performed by the healthcare representative 124 when constructing a new formulary. The healthcare representative 124 first accesses the central computer system 118 of the prescription coverage provider 110 at step S600. This can be accomplished in various ways. As previously discussed, it is possible for the healthcare representative 124 to meet with a CAE 112 to define their needs and identify products that will be covered by the formulary. Alternatively, such a meeting can take place using a conventional communication network. Under such circumstances, it is possible for the healthcare representative 124 to remotely access the central computer system 118 using one of the network connections previously defined. At step S610, the healthcare representative 124 reviews the various categories to identify whether products contained therein will be covered by the formulary. This steps also includes review of any and all subcategories contained within a category and subsequent subcategories. At step S612, the products to be covered by the formulary are selected. At step S614, the healthcare representative 124 optionally defines dosage limitations to associate with various products that have been selected. Similarly, at step S616, various delivery limitations can optionally be defined.

At step S618, it is determined whether the selected products are satisfactory for coverage by the formulary. If the healthcare provider 124 is not satisfied, then control returns to step S610 where the categories are again reviewed. If the healthcare representative 124 is satisfied with the selections, then control passes to step S620. At step S620, it is determined whether non-formulary products should be covered under any circumstances. If the healthcare representative 124 does not wish to cover non-formulary products then the process ends. Alternatively, if certain types of coverage will be offered for products not normally supported by the formulary, then control passes to step S622. At this point, the healthcare representative 124 would define all the special rules and limitations that can be used to cover a non-formulary product. As previously discussed, such rules can include varying types of copay selection of a generic brand rather than a name brand, limiting the dosage level of a name brand product, etc. Once the inclusion rules have been defined the process ends.

Figure 7:
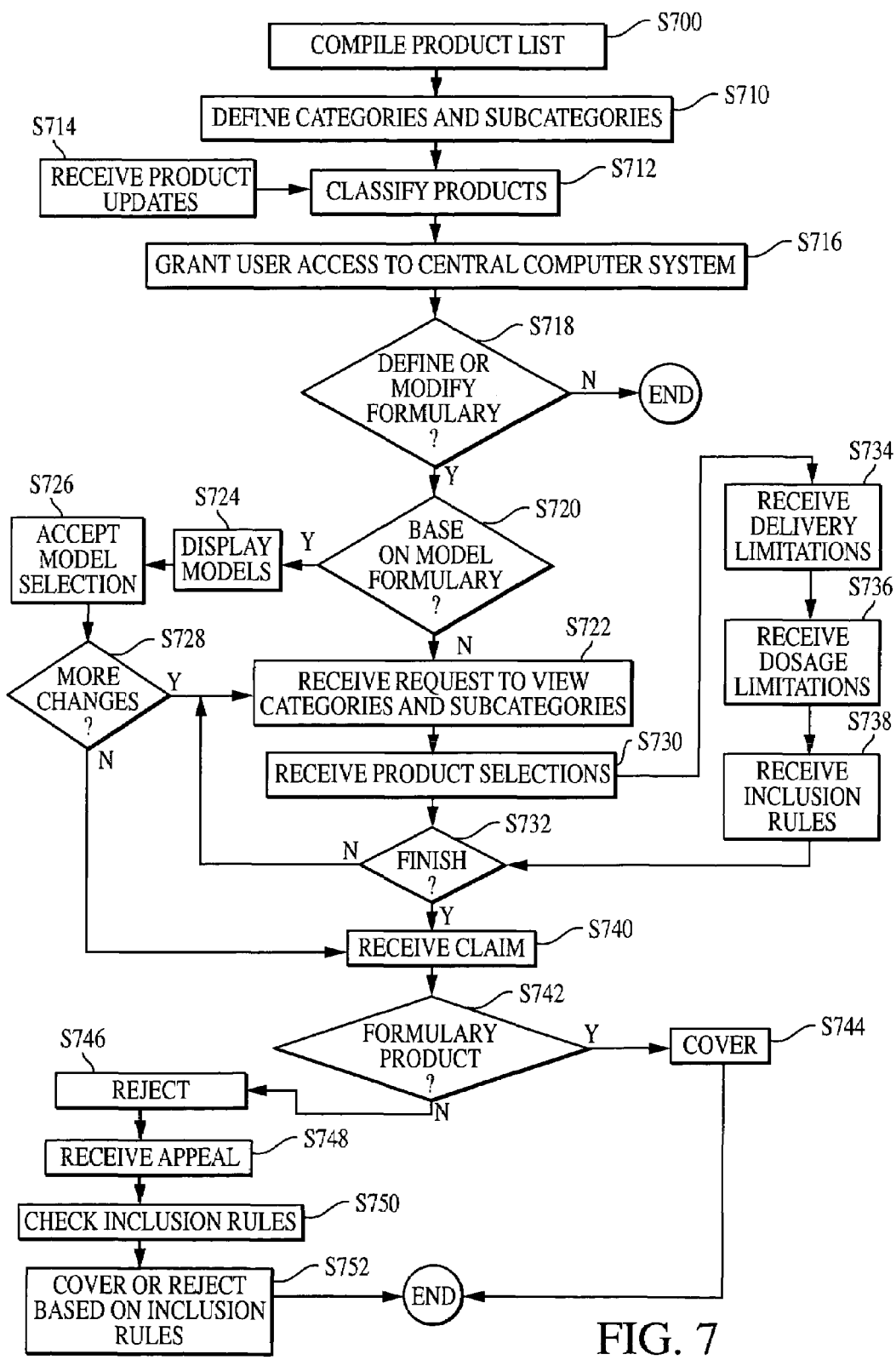
FIG. 7 is a flow chart outlining the steps performed by the prescription coverage provide when processing and implementing a formulary.

FIG. 7 details the steps performed by the prescription coverage provider when constructing and applying a particular formulary. At step S700, the product list is compiled. At step S710, the different categories and subcategories are defined. At step S712, the products are classified into the different categories and subcategories. As illustrated in FIG. 7, an optional step 714 receives product updates. This corresponds to the situation where the formulary has been completed and activated, but new products are released by the government agency. The updated products are then classified into the predefined categories and subcategories. At step S716, the healthcare provider 122 is granted access to the central computer system 118. As previously discussed, this can be done while the healthcare representative is meeting with the CAE 112, or through a connection across the electronic/communication network 130. At step S718, the healthcare representative 124 is prompted to indicate whether they would like to define a new formulary or modify an existing formulary. If the healthcare representative 124 replies in the negative, then the process ends. If the healthcare representative 124 would like to define or modify a formulary then control passes to step S720.

The healthcare representative 124 is queried to indicate whether they would like to define a new formulary based on an existing model (e.g., template) or modify an existing formulary. For example, an existing formulary can be modified to better suit the healthcare provider 122, or it can be modified to better correspond with a model formulary. If the healthcare representative 124 responds in the negative (e.g., they will not base the new formulary on an existing model), they must submit a request to view the categories and subcategories. If the healthcare representative 124 would like to base the formulary on an existing model, then at step S724, the existing models are displayed for review. At step S726, the central computer system 118 accepts the model selected by the healthcare representative 124. At step S728, the healthcare representative 124 is prompted to indicate if they would like to incorporate any changes to the model formulary. If no changes are required, then control passes the step S740. If additional changes are required or if the healthcare representative 124 indicated that they did not wish to base their formulary on a model then control passes to step S722.

The central computer receives a request to view the categories and subcategories from the healthcare representative 124. At step S730, the central computer system 118 receives product selections from the categories and subcategories. At step S732, the central computer system 118 prompts the healthcare representative 124 to indicate whether they are satisfied with the products currently covered by the formulary. This can involve, for example having the healthcare representative 124 review the current formulary to ensure that all their needs have been met. If the healthcare representative 124 is not satisfied, then control returns to step S722. Optionally, upon receiving the product selections, the healthcare representative 124 can also submit delivery limitations which are received at step S734. At step S736, the central computer system 118 would receive dosage limitations from the healthcare representative 124. At step S738, the central computer system 118 receives inclusion rules for the various products. Once the healthcare representative 124 is satisfied with the status of the formulary, it can be activated. At this point, the central computer system 118 is ready to receive and process claims based on the healthcare provider's requirements.

At step S740, a claim is received. At step S742 the central computer system 118 determines if the product in the claim is a formulary product. In other words the central computer system 118 reviews the formulary to determine if the healthcare provider 124 has included the product for coverage. If the product is a formulary product, then control passes to step S744 and coverage is granted. If the central computer system 118 determines that the product is not a formulary product, then the claim is rejected at step S746. At step S748, the central computer system 118 optionally receives an appeal for the rejected claim. At step S750, the central computer system 118 checks to see if there are any inclusion rules that would allow coverage of the rejected product. At step S752 the central computer system either covers or rejects the claim based on whether or not an applicable inclusion rule exists. The process then ends. It should be further noted that as previously described, the central computer system can optionally collect various data pertaining to construction and processing of the formulary. This data is collected throughout the process and can be used to subsequently define new model formularies and/or present information or suggestions to the healthcare provider 122.

Menu Arrangement

FIG. 8 illustrates an exemplary formulary setup menu according to an embodiment of the present invention. Such a menu can be displayed, for example, on the CAE's computer during the meeting with the healthcare representative 124 to construct the formulary. Alternatively, such a menu can be accessed by the healthcare representative 124 over the communication network 130 and displayed on the healthcare representative's computer 126. The formulary setup menu includes a graphical interface that allows the CAE 112 to access various information, and also includes fields for entering information and making selections. For example, a plurality of selection buttons 140 are provided to quickly perform certain acts such as saving the current file, clearing all fields, etc. Tabs 142 are provided to quickly bring different pages to the forefront and enter desired information.

As shown in FIG. 8, there are a plurality of fields 144 that allows the CAE 112 to customize identification criteria for the formulary. For example, the client name and contact name (e.g., the healthcare provider and healthcare representative) can be entered as well as a particular name for the formulary. The CAE 112 can also select, using an identification button 146, whether the formulary will be based on an existing model formulary that is standard in the prescription coverage provider's database, an existing formulary that the healthcare provider 122 has previously created, and an entirely new formulary. The setup menu also includes a comment field that allows the CAE 112 to enter various comments during the meeting with the healthcare representative 124. As previously discussed, such comments can be accessed from multiple points within the formulary design/access screens.

FIG. 9 illustrates a sample category listing according to one embodiment of the present invention. The listing includes sixteen category types 150 intended to cover all pharmaceutical products that may be selected for use in the formulary. Each category listing also includes a subcategory indicator 152, which gives a visual indication of whether there are subcategories which currently exist within the category.

FIG. 10 illustrates the hierarchy structure of the categories according to an exemplary embodiment of the present invention. As previously discussed, each category includes a subcategory indicator 152 that identifies whether there are collapsed subcategories that exist within the associated category. For example, subcategory indicator 152(A) provides a visual indication that subcategories exist within category 2, which contains antineoplastic and immunosuppressant drugs. Subcategory indicator 152(B) indicates that there are no collapsed subcategories within category 3 (e.g., all collapsed branches have been expanded). The subcategories, and optionally the categories, can further include selection indicators 154. The selection indicators 154 provide a visual display to the CAE 112, or healthcare representative 124, indicating whether or not products contained in the categories and subcategories have been selected for coverage by the formulary. For example, the selection indicator 154 can be in the form of a checkmark indicating that all products in the categories and subcategories have been selected for coverage by the formulary. Alternatively, the selection indicator 154 can be in the form of an "X" or the letter "N" to indicate that none of the products contained in the related categories and/or subcategories have been selected for coverage by the formulary. It is also possible to leave the selection indicator 154 blank to indicate that none of the products have been selected. The selection indicator 154 can optionally contain the letter "M" to indicate that there exists a mix of selected and nonselected products within the categories and subcategories contained in the associated category. Furthermore, the CAE 112 has an option to include an entire generic classification (e.g., an HICL classification), certain forms of a generic classification, brand name, brand name within a certain form, etc. for coverage by the formulary.

Figure 11:
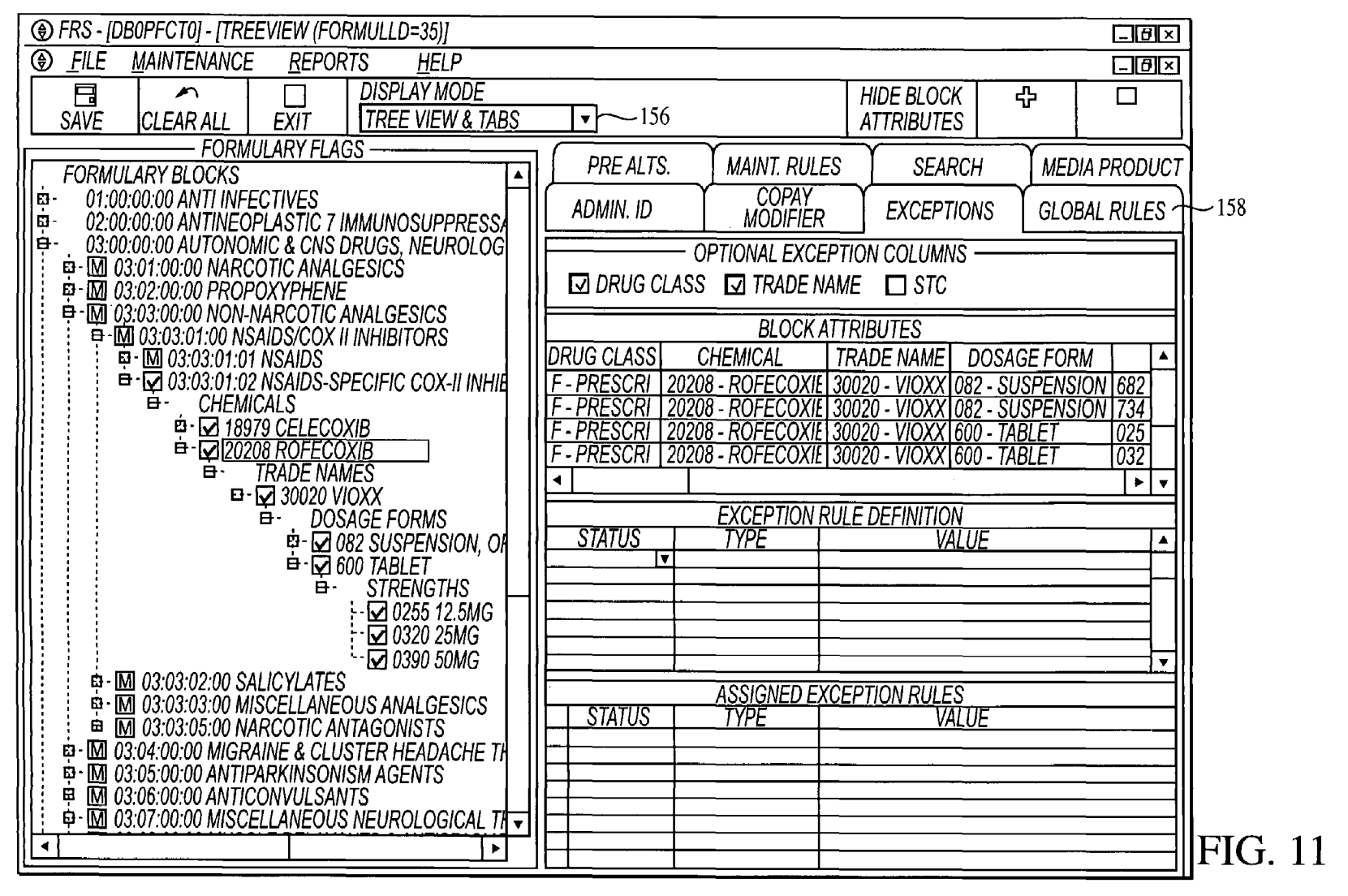

FIG. 11 illustrates a sample menu for defining inclusion rules. The CAE 112 can access this menu 156, for example, by selecting the display mode pull-down menu 156 and identifying the appropriate view. Such a selection would split the screen between the category tree and the selections tabs. The CAE 112 could then access the appropriate selection tab 158 to define the particular inclusion rule for a product, subcategory, or category highlighted in the formulary tree view. Selection tabs can also be used to define optional rules such as the level of copay that a patient would be obligated to provide, global rules to be applied to all products covered by the formulary, the manner in which newly received files are maintained (maintenance rules), preferred alternatives, media products, etc. The media products can, for example, correspond to digitized video and/or audio files that can be played for the healthcare representative 124. Alternatively, the audio and video files can be accessed across the communication network 130 and played on the healthcare representative's computer 126.

FIG. 12 illustrates a sample menu for defining delivery limitations. The menu provides a plurality of columns (three in this example) that are used to define various characteristics for limiting the delivery of certain products. For example, the first column 160 is used to identify the particular rule. The second column 162 gives a description of the delivery method. For example, the product can be in the form of various types of aerosols, implants, inhalants, etc. The third column 164 is a status column that allows the CAE 112 to indicate whether or not the particular delivery method will be supported by the formulary.

Hardware Overview

Figure 13:
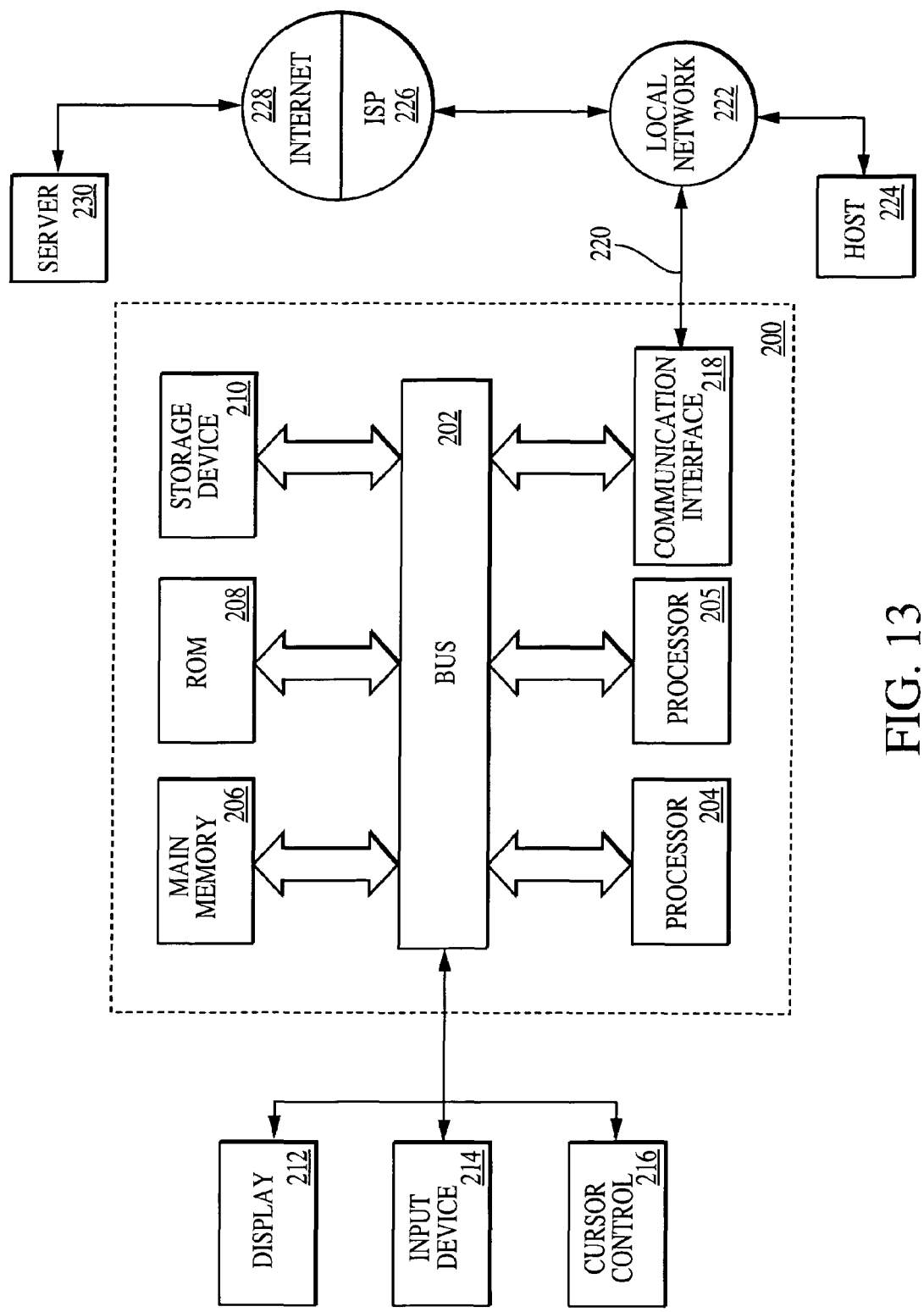
FIG. 13 is a block diagram illustrating an exemplary computer system for implementing an embodiment of the present invention.

FIG. 13 is a block diagram that illustrates a computer system 200 upon which an embodiment of the invention may be implemented. Computer system 200 includes a bus 202 or other communication mechanism for communicating information, and a processor 204 coupled with bus 202 for processing information. Computer system 200 also includes a main memory 206, such as a random access memory (RAM) or other dynamic storage device, coupled to bus 202 for storing information and instructions to be executed by processor 204. Main memory 206 also may be used for storing temporary variables or other intermediate information during execution of instructions to be executed by processor 204. Computer system 200 further includes a read only memory (ROM) 208 or other static storage device coupled to bus 202 for storing static information and instructions for processor 204. A storage device 210, such as a magnetic disk or optical disk, is provided and coupled to bus 202 for storing information and instructions.

Computer system 200 may be coupled via bus 202 to a display 212, such as a cathode ray tube (CRT), for displaying information to a computer user. An input device 214, including alphanumeric and other keys, is coupled to bus 202 for communicating information and command selections to processor 204. Another type of user input device is cursor control 216, such as a mouse, a trackball, or cursor direction keys for communicating direction information and command selections to processor 204 and for controlling cursor movement on display 212. This input device typically has two degrees of freedom in two axes, a first axis (e.g., x) and a second axis (e.g., y), that allows the device to specify positions in a plane.

The invention is related to the use of computer system 200 for managing prescription benefits. According to one embodiment of the invention, managing prescription benefits is provided by computer system 200 in response to processor 204 executing one or more sequences of one or more instructions contained in main memory 206. Such instructions may be read into main memory 206 from another computer-readable medium, such as storage device 210. Execution of the sequences of instructions contained in main memory 206 causes processor 204 to perform the process steps described herein. One or more processors in a multi-processing arrangement may also be employed to execute the sequences of instructions contained in main memory 206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 204 for execution. Such a medium may take many forms, including but not limited to, non-volatile media, volatile media, and transmission media. Non-volatile media include, for example, optical or magnetic disks, such as storage device 210. Volatile media include dynamic memory, such as main memory 206. Transmission media include coaxial cables, copper wire and fiber optics, including the wires that comprise bus 202. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 204 for execution. For example, the instructions may initially be borne on a magnetic disk of a remote computer. The remote computer can load the instructions into its dynamic memory and send the instructions over a telephone line using a modem. A modem local to computer system 200 can receive the data on the telephone line and use an infrared transmitter to convert the data to an infrared signal. An infrared detector coupled to bus 202 can receive the data carried in the infrared signal and place the data on bus 202. Bus 202 carries the data to main memory 206, from which processor 204 retrieves and executes the instructions. The instructions received by main memory 206 may optionally be stored on storage device 210 either before or after execution by processor 204.

Computer system 200 also includes a communication interface 218 coupled to bus 202. Communication interface 218 provides a two-way data communication coupling to a network link 220 that is connected to a local network 222. For example, communication interface 218 may be an integrated services digital network (ISDN) card or a modem to provide a data communication connection to a corresponding type of telephone line. As another example, communication interface 218 may be a local area network (LAN) card to provide a data communication connection to a compatible LAN. Wireless links may also be implemented. In any such implementation, communication interface 218 sends and receives electrical, electromagnetic or optical signals that carry digital data streams representing various types of information.

Network link 220 typically provides data communication through one or more networks to other data devices. For example, network link 220 may provide a connection through local network 222 to a host computer 224 or to data equipment operated by an Internet Service Provider (ISP) 226. ISP 226 in turn provides data communication services through the worldwide packet data communication network, now commonly referred to as the "Internet" 228. Local network 222 and Internet 228 both use electrical, electromagnetic or optical signals that carry digital data streams. The signals through the various networks and the signals on network link 220 and through communication interface 218, which carry the digital data to and from computer system 200, are exemplary forms of carrier waves transporting the information.

Computer system 200 can send messages and receive data, including program code, through the network(s), network link 220, and communication interface 218. In the Internet example, a server 230 might transmit a requested code for an application program through Internet 228, ISP 226, local network 222 and communication interface 218. In accordance with the invention, one such downloaded application provides for managing prescription benefits as described herein. The received code may be executed by processor 204 as it is received, and/or stored in storage device 210, or other non-volatile storage for later execution. In this manner, computer system 200 may obtain application code in the form of a carrier wave.

Major objectives and advantages of the present invention are expediency and cost reduction (where appropriate). The formulary rulestation benefits healthcare providers, patents and pharmacists. More particularly, healthcare providers can quickly and efficiently create formularies for multiple prescription coverage plans. This results in increased variety and selection to patients. Healthcare providers can also minimize the cost of coverage by defining base, or template, formularies, which include major products that will be covered by all formularies. The template formularies can be independently modified to further cover specialized products required by clients. Accordingly, the time required create a new formulary can be further reduced. Temporary versions of a formulary can be quickly and easily saved in a network environment or circulated on computer media to different personnel for review, modification, approval, electronic signature, etc. Reports can be generated based on individual formularies or across multiple formularies for a healthcare provider, geographical region, etc. Patients benefit from having a choice in selecting the prescription coverage plans tailored to best suit their needs. This choice further results in reduced costs to the patient. For example, if a patient is not allergic to certain products and/or does not mind receiving generic forms of a product, then a less expensive formulary may best suit their coverage needs. Furthermore, costs are reduced because of improved efficiency realized by the prescription coverage provider and pharmacist.

The present invention provides various benefits including an apparatus an method for efficiently creating, modifying, and maintaining formularies associated with different prescription coverage plans and/or modify formularies. Rather than programming individual subroutines, modules, applets, etc. for each formulary, the present invention can be optionally implemented as a formulary rulestation which provides a content-based interface for allowing quick and flexible selection of individual drugs (e.g., products) and/or drug classes (e.g., categories) while creating a formulary. The present invention can also implemented as a rule-based system, thereby eliminating the need to manually select and reject individual drugs from the NDC listings. Accordingly, formularies can be quickly viewed, revised, and approved.

Optional embodiments of the present invention include implementation on a computer having a graphical user interface such as the Windows™ series of operating systems, X-windows™, Mac™ OS, Linux, Unix, etc. Users can be presented with a variety of screens where information can be selected with a graphical input device such as a mouse or light pen. Additionally, a standard user interface such as a keyboard can be used to input textual information. Each screen can be configured to present the user with various options for creating/modifying a formulary, selecting specific drugs, defining copay rules, etc. The screens can include one or more pull-down menus that reveal hidden features/options to the user. Furthermore, display tabs can be used to quickly select and quickly bring a particular screen to the forefront.

Such implementations allow creation of formularies by simply selecting appropriate options and navigating through the graphical interface. For example, a user can begin the process by selecting the option for creating a new formulary. The user would then be requested to input a unique name or title for the new formulary. Further options include a hierarchical organization of products in a tree structure having sixteen (16) therapeutic chapters at the highest level. The sixteen chapters encompass all (or substantially all) existing drugs, chemicals, agents, etc. currently available in the United States. For example, one of the-chapters can be designated anti-infectives. Navigation through the anti-infective branch would reveal different types of anti-infectives such as anti-virals, penicillins, tetracyclines, etc. Subsequent navigation would reveal further sub-classifications. Such a hierarchical organization provides a high level of granularity and allows all drugs identified by the NDC to be incorporated into the formulary rulestation. Accordingly a CAE has a great degree of flexibility in designing formularies for healthcare providers.

Formularies can be quickly and efficiently created by simply selecting each desired product within the system. Furthermore, groups (or classes) of a particular product can be simultaneously included or excluded with a single selection. Such a feature can significantly reduce the amount of time required to create a formulary by eliminating the need to individually include or exclude each drug. The present invention can optionally provide a visual indication of the selection status of products within a collapsed branch by including, for example, a "Y", "N", or "M" label corresponding to yes, no, and mixed, respectively. Alternatively, various color combinations or symbols can be used to provide similar indications. Users can optionally input notes and/or comments for different products, categories, etc. as a formulary is being developed. One benefit of such a feature is that a user is not required to retrace navigation steps in order to review, revise, or otherwise recall the content of their notes. Furthermore, all notes taken during a meeting can be reviewed as a single entry which is dynamically updated.

The present invention can optionally provide product linking within a formulary. More particularly, a formulary can include hypertext links to other sources of information such as media, text, etc. The information can be stored in various locations, including other computers, network servers, the Internet, etc. For example, a healthcare provider reviewing a formulary can select a hypertext link that presents a video or audio clip describing side effects or benefits of a particular product. The hypertext link can likewise present a text summary of the side effects or benefits of the same product.

Security restrictions can be optionally provided to control accessibility to certain features of the system. For example, all users (or potential users) can be given a password or access code. The password can be used to automatically limit the information viewable by the user. The information that can be changed and/or deleted by the user would also be restricted. For example, access to information could be restricted depending on the particular user (e.g., CAE, Formulary Operations, etc.). Furthermore, CAEs can limit another user's ability to modify a formulary that is currently under development for a healthcare provider. Once a CAE creates a formulary, their identification can be automatically associated with that formulary. In such a situation, the CAE would be the only user capable of modifying the formulary. The CAE can also designate backup users that can have full access to the formulary. Such a configuration is beneficial for situations where the healthcare provider urgently requires changes to the formulary, but the CAE is not available. Accordingly, one of the backup users can consult with the healthcare provider and perform the necessary changes to the formulary.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of constructing a formulary, comprising:
   (a) storing a plurality of pharmaceutical products in a computer;
   (b) storing in the computer a plurality of pharmaceutical categories, wherein each pharmaceutical category comprises:
      (i) a category definition based on predetermined relational characteristics shared by the plurality of pharmaceutical products;
      (ii) a therapeutic description;
   (c) sorting, by the computer, the plurality of pharmaceutical products into the appropriate pharmaceutical category based on each pharmaceutical product's matching with individual category definitions and therapeutic descriptions for the respective pharmaceutical category;
   (d) displaying, by the computer, the sorted plurality of pharmaceutical products, wherein each pharmaceutical product is classified into at least one pharmaceutical category,
   (e) creating a plurality of base formularies, wherein each base formulary is created by:
      (i) selecting on the computer at least one of the sorted pharmaceutical products for inclusion in the base formulary,
      (ii) entering into the computer inclusion rules descriptive of the base formulary;
      (iii) saving the base formulary in the computer,
   (f) creating a new formulary by:
      (i) defining desired inclusion rules comprising criteria for accepting coverage of non-formulary pharmaceutical products when present;
      (ii) selecting at least one of the preexisting base formularies when the selected base formulary's inclusion rules are substantially similar to the desired inclusion rules by:
         (1) displaying to the user information for selection of the base formulary and respective inclusion rules;
         (2) allowing the user to select using the computer the preexisting base formulary responsive to said prompting;
      (iii) modifying the selected base formulary when additional pharmaceutical products are present by allowing the user to select on the computer the additional pharmaceutical products to be included into the new formulary;
      (iv) saving when the selected base formulary is modified in the computer as the new formulary;
   (g) adding the new formulary for use by the user to administer a pharmaceutical benefits plan for a plurality of members.

2. The method of claim 1, wherein the step of sorting comprises sorting the pharmaceutical products into sixteen defined categories based on predetermined relational characteristics.

3. The method of claim 2, wherein the sixteen categories are selected from a group comprising anti-infectives; antineoplastic and immunosuppressant drugs; autonomic and central nervous system drugs, neurology and psychiatry; cardiovascular, hypertension and lipids; dermatological and/or topical therapy; ear, nose and throat medications; endocrine and/or diabetes; gastroenterology; immunology, vaccines and biotechnology; musculoskeletal and rheumatology; obstetrics and gynecology; ophthalmology; respiratory, allergy, cough and cold; urologicals; vitamins, hematinics and electrolytes; and diagnostics and miscellaneous agents.

4. The method of claim 3, further comprising a step of linking pharmaceutical products to information sources.

5. The method of claim 4, wherein the step of linking includes a step of creating a hypertext link to the information sources.

6. The method of claim 4, wherein the information sources are remotely located.

7. The method of claim 3, further comprising the steps:
collecting data pertaining to claims processing during implementation of the formulary; and
preparing a budgetary analysis for the cost of implementing the formulary, based at least in part on the number of prescription claims accepted for coverage and an associated coverage cost.

8. The method of claim 7, wherein a prescription claim has been rejected and further comprising the step of:
appealing rejection of the prescription claim, and
wherein the step of preparing is further performed based on a cost of processing the appeal.

9. The method of claim 3, further comprising a step of creating a model formulary based at least in part on prescription claims that have been accepted for coverage and prescription claims that have been rejected for coverage.

10. The method of claim 3, further comprising the steps:
automatically updating the list of pharmaceutical products at predetermined intervals to include newly released pharmaceutical products; and
sorting the newly released pharmaceutical products into the at least one pharmaceutical categories based on the predetermined relational characteristics.

11. The method of claim 3, wherein:
the at least one pharmaceutical category includes at least one subcategory; and
the step of sorting comprises a step of sorting the pharmaceutical products into the at least one category and the at least one subcategory.

12. The method of claim 3, wherein the step of creating a plurality of base formularies further comprises the steps:
receiving a selection for a category; and
automatically including all pharmaceutical products contained in the selected category and all pharmaceutical products contained in the at least one subcategory contained in the selected category.

13. The method of claim 3, further comprising a step of indicating a selection status for pharmaceutical products in the at least one category.

14. The method of claim 3, further comprising a step of automatically selecting newly released pharmaceutical products to be supported by the formulary, based at least in part on the categories where the newly released pharmaceutical products are sorted.

15. The method of claim 3, further comprising a step of establishing global rules to be applied to the formulary when performing the steps of selecting, accepting, and rejecting.

16. The method of claim 1, further comprising a step of defining dosage limitations for the pharmaceutical products supported by the formulary.

17. The method of claim 16, wherein the dosage limitations are selected from at least one of strength of the pharmaceutical products per dose and time release.

18. The method of claim 1, further comprising a step of defining delivery limitations for the pharmaceutical products supported by the formulary.

19. The method of claim 18, wherein in the delivery limitations are selected from the group of delivery methods consisting of topical, oral, and injectionable.

20. The method of claim 1, further comprising a step of indicating a selection status for pharmaceutical products in the at least one pharmaceutical category.

21. The method of claim 20, wherein the step of indicating comprises a step of indicating whether all pharmaceutical products in the at least one pharmaceutical category have been selected or have not been selected, or indicating whether only some of the pharmaceutical products have been selected.

22. The method claim 1, further comprising a step of indicating whether each of the at least one pharmaceutical category of the plurality of pharmaceutical categories contains subcategories.

23. The method of claim 22, further comprising a step of indicating whether each of the at least one subcategory contains additional subcategories.

24. The method of claim 1, further comprising a step of linking pharmaceutical products to information sources.

25. The method of claim 24, wherein the step of linking includes a step of creating a hypertext link to the information sources.

26. The method of claim 1, wherein the step of selecting at least one of the sorted pharmaceutical products further comprises a step of establishing global rules to be applied to the formulary.

27. The method of claim 1, wherein the inclusion rules further defines a copay value that is greater than a formulary copay.

28. The method of claim 1, wherein the inclusion rules further defines pre-authorization procedures for accepting coverage of the non-formulary pharmaceuticals.

29. The method of claim 1, wherein the step of defining desired inclusion rules includes a step of suggesting at least one preferred alternative pharmaceutical product that would be covered by the prescription formulary.

30. The method of claim 1, further comprising a step of creating reports that compare two or more formularies.

31. The method of claim 1, wherein:
the at least one pharmaceutical category includes at least one subcategory; and
the step of sorting comprises a step of sorting the pharmaceutical products into the at least one pharmaceutical category and the at least one subcategory.

32. The method of claim 1, wherein the step of selecting includes a step of selecting a plurality of pharmaceutical products over an electronic network.

33. The method of claim 1, further comprising the step of preparing a budgetary analysis comprising cost for covering the pharmaceutical products provided by the formulary.

34. The method of claim 1, wherein the type of coverage is defined by a budgetary analysis.

35. The method of claim 1, wherein the type of coverage provides optimum coverage at low cost.

36. A method of constructing a formulary, comprising:
(a) storing a plurality of pharmaceutical products in a computer;
(b) storing in the computer a plurality of pharmaceutical categories, wherein each pharmaceutical category comprises:
  (i) a category definition based on predetermined relational characteristics shared by the plurality of pharmaceutical products;
  (ii) a therapeutic description;
(c) sorting, by the computer, the plurality of pharmaceutical products into the appropriate pharmaceutical category based on each pharmaceutical product's matching with individual category definitions and therapeutic descriptions for the respective pharmaceutical category;
(d) displaying, by the computer, the sorted plurality of pharmaceutical products, wherein each pharmaceutical product is classified into at least one pharmaceutical category,
(e) creating a plurality of base formularies, wherein each base formulary is created by:
  (i) selecting on the computer at least one of the sorted pharmaceutical products for inclusion in the base formulary,
  (ii) entering into the computer inclusion rules descriptive of the base formulary;
  (iii) saving the base formulary in the computer,
(f) updating the list of pharmaceutical products in at least one of the plurality of base formularies at predetermined intervals to include newly released pharmaceutical products;
(g) sorting the newly released pharmaceutical products into the at least one categories based on the predetermined relational characteristics;
(h) selecting additional released pharmaceutical products from the newly released pharmaceutical products to be supported by the at least one of the plurality of formularies, based at least in part on the categories where the newly released pharmaceutical products are sorted;
(i) receiving a prescription claim for coverage of a prescribed pharmaceutical product,
(j) accepting coverage for the prescription claim based on whether the prescribed pharmaceutical product is supported by at least one of the formularies, and
(k) rejecting coverage for the prescription claim based on whether the prescribed pharmaceutical product is not supported by the at least one of the formularies.

* * * * *

UNITED STATES PATENT AND TRADEMARK OFFICE
CERTIFICATE OF CORRECTION

PATENT NO.         : 7,490,047 B2  
APPLICATION NO.    : 10/337366  
DATED              : February 10, 2009  
INVENTOR(S)        : Brown et al.

Page 1 of 1

It is certified that error appears in the above-identified patent and that said Letters Patent is hereby corrected as shown below:

Title Page;

On the Letters Patent Cover Sheet:

On Column 2, Item 57 – Abstract, line 12, please change "die" to -- the --.

Signed and Sealed this

Seventh Day of April, 2009

JOHN DOLL  
*Acting Director of the United States Patent and Trademark Office*